US012025606B2

(12) United States Patent
Locklear et al.

(10) Patent No.: US 12,025,606 B2
(45) Date of Patent: Jul. 2, 2024

(54) DETERMINATION OF CHLORIDE CONCENTRATION IN DRILLING FLUIDS

(71) Applicant: CONOCOPHILLIPS COMPANY, Houston, TX (US)

(72) Inventors: Jay Locklear, Houston, TX (US); Molly Merritt, Tulsa, OK (US)

(73) Assignee: CONOCOPHILLIPS COMPANY, Houston, TX (US)

( * ) Notice: Subject to any disclaimer, the term of this patent is extended or adjusted under 35 U.S.C. 154(b) by 0 days.

(21) Appl. No.: 17/746,077

(22) Filed: May 17, 2022

(65) Prior Publication Data

US 2022/0373531 A1 Nov. 24, 2022

Related U.S. Application Data

(60) Provisional application No. 63/190,085, filed on May 18, 2021.

(51) Int. Cl.
G01N 33/28 (2006.01)
G01N 27/06 (2006.01)

(52) U.S. Cl.
CPC ......... *G01N 33/2823* (2013.01); *G01N 27/06* (2013.01)

(58) Field of Classification Search
CPC ............................ G01N 33/2823; G01N 27/06
See application file for complete search history.

(56) References Cited

U.S. PATENT DOCUMENTS

| 2013/0074910 | A1* | 3/2013 | Isoue | B32B 17/10605 524/308 |
| 2014/0150866 | A1* | 6/2014 | Muguruma | B32B 17/10036 428/437 |
| 2014/0352948 | A1 | 12/2014 | Barral et al. | |
| 2018/0230761 | A1 | 8/2018 | Sehsah | |
| 2019/0227048 | A1 | 7/2019 | Ye et al. | |
| 2021/0025842 | A1* | 1/2021 | Hawsah | B01J 38/52 |

OTHER PUBLICATIONS

Valdivia, et al—Conductometric Titration of Metformin Hydrochloride: Simulation and Experimentation, 2019, J. Chem. Chem Eng., vol. 13, pp. 105-111.
www.metrohm.com/en-us/products-overview/tritration/eco-tritrator/ 210083010.
Kaland, F, et al—"US of an Ion-Selective Electrode for Determination of Free Chloride Ions in Water-Based Drilling Fluids", 1986, SPE Drilling Engineering, pp. 365-368; 4 pgs.
Anderson, Lloyd J., Conductometric Titration of Chloride in Sea Water and Marine Sediments, Scripps Institutional of Oceanography, La Jolla, CA 1948; 2 pgs.

* cited by examiner

*Primary Examiner* — Christopher P McAndrew
*Assistant Examiner* — Zannatul Ferdous
(74) *Attorney, Agent, or Firm* — CONOCOPHILLIPS COMPANY

(57) ABSTRACT

The invention relates to a system and method for analyzing drilling fluid from a drilling rig for accessing subterranean hydrocarbons. The system and method involve analysis for chloride by replacing conventional chemical titration with electrical conductivity titration.

14 Claims, 2 Drawing Sheets

DETERMINATION OF CHLORIDE CONCENTRATION IN DRILLING FLUIDS

CROSS-REFERENCE TO RELATED APPLICATIONS

This application is a non-provisional application which claims benefit under 35 USC § 119(e) to U.S. Provisional Application Ser. No. 63/190,085 filed May 18, 2021, entitled "Determination of Chloride Concentration in Drilling Fluids," which is incorporated herein in its entirety.

STATEMENT REGARDING FEDERALLY SPONSORED RESEARCH

None.

FIELD OF THE INVENTION

This invention relates to the determination of chloride content in drilling fluids, such as in oil-based or synthetic-based drilling fluid or drilling mud.

BACKGROUND OF THE INVENTION

The current method of measuring whole mud chlorides in drilling fluids, including oil-based drilling fluid is dependent on the indicator chemical potassium chromate.

For oil based fluids, a small sample of oil-based mud is mixed with a solvent, e.g. Propylene Glycol, n-Propyl Ether (PNP) or Isopropyl Alcohol (IPA)/Xylene to break the emulsion. The sample is then diluted with distilled water and the indicator solution is added turning the sample slightly yellow. Silver nitrate is titrated until the sample turns pink indicating the endpoint has been reached. The amount of silver nitrate titrated to change the sample from yellow to pink is used to calculate the amount of chloride present.

Testing for chloride in drilling fluid is often conducted in the field in the harsh environment of an oil rig. Oil-based drilling mud is a challenging medium in which to perform a test for a particular ion, firstly because of being oil-based but also due to the large concentration of particulates and also for the presence of many impurities from downhole. Color change titration using potassium chromate has proven to be a robust and quick procedure well suited to these challenges. However, potassium chromate is a potentially hazardous chemical and therefore an alternative method for measuring the chloride concentration in drilling fluid is desirable. Furthermore, in certain drilling fluids, the potassium chromate color change can be hard to observe and this can lead to unacceptable inaccuracies.

BRIEF SUMMARY OF THE DISCLOSURE

The invention more particularly includes a method and apparatus for determining the chloride concentration in drilling fluid in accordance with the appended claims, which also set out optional features of the invention.

The inventors have explored a number of alternative ways of measuring chloride concentration in oil-based drilling fluid. These included using commercially available equipment designed for analysis of oil based drilling fluid, but which was found to be ineffective at analyzing for chloride.

Initially, the inventors evaluated the effectiveness of using an ion-specific electrode (ISE) probe and meter to measure the chloride ion concentration. An ISE probe is a transducer that converts the activity of a specific ion dissolved in a solution into an electrical potential. The voltage is dependent on the logarithm of the ionic activity. Prior to measurement, the meter is calibrated with standards of known concentrations varying by tenfold (e.g. 10, 100, 1000 ppm).

Brines were made from sodium chloride (NaCl), potassium chloride (KCl), and calcium chloride ($CaCl_2$). Dilutions of each of the brines were made to cover a range from 1 to 980 ppm to determine the accuracy of the ISE probe's response over a wide range of concentrations. The results from the sodium chloride test were used to set calibration points prior to measuring chloride concentration in potassium chloride and calcium chloride brines. The potassium chloride solutions yielded very good results with only the low-end concentrations reading above the allowable error range (±10%); however, the calcium chloride solutions yielded highly inaccurate results ranging from 30-90% error. Brines were prepared with magnesium chloride ($MgCl_2$) and strontium chloride ($SrCl_2$) to determine if the divalent cation was potentially causing issues. Results from the diluted $MgCl_2$ and $SrCl_2$ solutions yielded satisfactory results with more erroneous values also coming from the low-end concentrations.

In many oil based mud formulations, calcium chloride brine is emulsified (internal phase) into the fluid system in addition to containing other calcium additives such as lime (CaO or $Ca(OH)_2$). Additional sources of calcium in oil based muds can include drilled solids such as gypsum ($CaSO_4 \cdot 2H_2O$) and anhydrite ($CaSO_4$). In certain oil reservoirs, for example in the North Sea, the formation rock is calcium carbonate ($CaCO_3$) and this can also be a source of calcium ions in the mud. There is therefore a high concentration of calcium ions in most oil based muds. Since the calcium cation was causing a strong interference with the ISE reading output, and without the error being predictable (i.e. no correction factor could be determined), the inventors discarded this method of measuring the chloride ion concentration.

Since calcium is so prevalent, a possible approach would be to titrate for calcium ions and base an estimate of chloride ion concentration on this value. Thus, a standard calcium titration could be used for calculating the whole mud chlorides, using an assumption that all calcium is from calcium chloride. The inventors used the standard titration API RP13B-2. This is American Petroleum Institute Recommended Practice for Field Testing Oil-Based Drilling Fluids ($5^{th}$ edition, 2014); Section 10.6 relates to whole-drilling-fluid calcium analysis. The inventors believe this approach may be acceptable for day to day use, but of course it does not measure chloride directly and the proportion of chloride from calcium chloride vs. chloride from other compounds such as sodium chloride may vary. Accordingly, the inventors believe that a chloride specific test may also need to be used regularly to supplement the calcium ion test. A chloride ion test may also need to be used if a significant change in calcium ion concentration or water fraction is observed.

The inventors have found that chloride concentration measurements with a conductivity probe proved accurate and repeatable with a variety of brines and oil-based muds. A procedure similar to the potassium chromate titration was followed, except the conductivity data was measured with incremental additions of silver nitrate. The chlorides endpoint was determined graphically by plotting the conductivity values against the volume of silver nitrate titrated into the sample or by calculation.

As chloride and silver ions are removed from solution as solid silver chloride, conductivity of the solution decreases due to the lower conductivity of nitrate ions compared to chloride ions. Once all chloride is removed, the conductivity rises due to increasing quantity of silver and nitrate ions in solution. If conductivity values are plotted, two straight lines are obtained and the intersection of the two slopes yields the value of silver nitrate to use in calculating the chloride ion concentration of the whole mud.

The process requires a substantial time for equalization after each addition of silver nitrate and is therefore potentially laborious and time-consuming for use in the field. However, it may be possible to automate the procedure and thereby provide a practical method and apparatus for use in the field. Automatic titration equipment for laboratory use is known, but the inventors are not aware of such equipment which is suitable for use in harsh environments.

The inventors believe that suitable equipment may require probes which have a polymer or metal protective body and at least one conductivity-detecting sensor within the protective body. It is preferred that the sensors have a plate configuration. One of the many challenges of testing in this environment is cleaning and it is important to be able to clean the sensors well. The plate configuration facilitates cleaning and general maintenance.

The inventors believe that suitable automatic titration apparatus may need to be adapted to function with probes having features as described above, and be equipped with a rugged casing and screen, controls, etc. adapted to a harsh environment rather than a laboratory.

The inventors believe the technique would be equally effective for water based muds.

Examples and various features and advantageous details thereof are explained more fully with reference to the exemplary, and therefore non-limiting, examples illustrated in the accompanying drawings and detailed in the following description. Descriptions of known starting materials and processes can be omitted so as not to unnecessarily obscure the disclosure in detail. It should be understood, however, that the detailed description and the specific examples, while indicating the preferred examples, are given by way of illustration only and not by way of limitation. Various substitutions, modifications, additions and/or rearrangements within the spirit and/or scope of the underlying inventive concept will become apparent to those skilled in the art from this disclosure.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited only those elements but can include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term substantially, as used herein, is defined to be essentially conforming to the particular dimension, shape or other word that substantially modifies, such that the component need not be exact. For example, substantially cylindrical means that the object resembles a cylinder, but can have one or more deviations from a true cylinder.

Additionally, any examples or illustrations given herein are not to be regarded in any way as restrictions on, limits to, or express definitions of, any term or terms with which they are utilized. Instead, these examples or illustrations are to be regarded as being described with respect to one particular example and as illustrative only. Those of ordinary skill in the art will appreciate that any term or terms with which these examples or illustrations are utilized encompass other examples as well as implementations and adaptations thereof which can or cannot be given therewith or elsewhere in the specification and all such examples are intended to be included within the scope of that term or terms. Language designating such non-limiting examples and illustrations includes, but is not limited to: "for example," "for instance," "e.g.," "In some examples," and the like.

Although the terms first, second, etc. can be used herein to describe various elements, components, regions, layers and/or sections, these elements, components, regions, layers and/or sections should not be limited by these terms. These terms are only used to distinguish one element, component, region, layer or section from another. Thus, a first element, component, region, layer or section discussed below could be termed a second element, component, region, layer or section without departing from the teachings of the present inventive concept.

While preferred examples of the present inventive concept have been shown and described herein, it will be obvious to those skilled in the art that such examples are provided by way of example only. Numerous variations, changes, and substitutions will now occur to those skilled in the art without departing from the disclosure. It should be understood that various alternatives to the examples of the disclosure described herein can be employed in practicing the disclosure. It is intended that the following claims define the scope of the disclosure and that methods and structures within the scope of these claims and their equivalents be covered thereby.

The term "oil based or synthetic based mud" shall be taken to mean a non-aqueous drilling fluid system comprising an external (continuous) phase that is either a (natural) oil (e.g. crude, diesel or mineral oil) or a synthetic (manufactured) hydrocarbon or other organic compound (e.g. esters or olefins).

BRIEF DESCRIPTION OF THE DRAWINGS

A more complete understanding of the present invention and benefits thereof may be acquired by referring to the following description taken in conjunction with the accompanying drawings in which.

DETAILED DESCRIPTION

The following examples of certain embodiments of the invention are given. Each example is provided by way of explanation of the invention, one of many embodiments of the invention, and the following examples should not be read to limit, or define, the scope of the invention.

Example 1—North Sea Oil Based Mud

While titrating the silver nitrate into the solution, and in the absence of the indicator solution, a conductivity probe is inserted into the solution. The conductivity is measured with incremental additions of silver nitrate as the titrant. Once the equivalence point is reached, the conductivity of the solution should increase rapidly as more titrant is added. Plotting the volume of silver nitrate (titrant) vs measured conductivity, two distinct lines are formed. The equivalence point can be determined by plotting the data, or it can be calculated from the slopes and y-axis intercepts of the two lines. This equivalence point value is then used to calculate the concentration of chlorides, just as is done with the potassium chromate titration.

For this laboratory study, a Mettler Toledo SevenExcellence benchtop conductivity meter was used with the Mettler Toledo InLab 741-ISM conductivity probe.

The probe was first tested using stock solutions of sodium chloride and calcium chloride, using standard procedures. Errors of less than 4% were recorded in each case.

First, an oil based mud from a North Sea drilling rig was tested. Identical tests in two of the applicant's laboratories were conducted.

The oil-based mud was prepared using the standard procedure provided by API for measuring whole mud chlorides, with the exception of potassium chromate. A few milliliters of sulfuric acid were added to the solution to get the pH below 7. This pH<7.0 step is a standard part of the API procedure. Silver nitrate was added in 0.5 mL increments and given 1-2 minutes to equilibrate before the conductivity of the sample was measured. The results are shown in Tables 1 and 2 below.

TABLE 1

| Results | |
|---|---|
| | mL |
| PNP | 100 |
| OBM | 2 |
| DI | 200 |
| Sulfuric Acid | 4 |

TABLE 2

North Sea Oil Based Mud

| mL AgNO$_3$ | Conductivity, μS/cm (1 min) | Conductivity, μS/cm (1 min) |
|---|---|---|
| 0 | 205.5 | 239.8 |
| 0.5 | 199.1 | 231.7 |
| 1.0 | 195.4 | 225.9 |
| 1.5 | 192.6 | 218.7 |
| 2.0 | 187.9 | 211.9 |
| 2.5 | 183.7 | 209.2 |
| 3.0 | 180.1 | 209.0 |
| 3.5 | 182.7 | 217.4 |
| 4.0 | 195.0 | 235.6 |
| 4.5 | 207.8 | 254.3 |
| 5.0 | 220.1 | 271.4 |
| 5.5 | 231.8 | 289.5 |
| 6.0 | 248.7 | 317.9 |

Figure 1A:
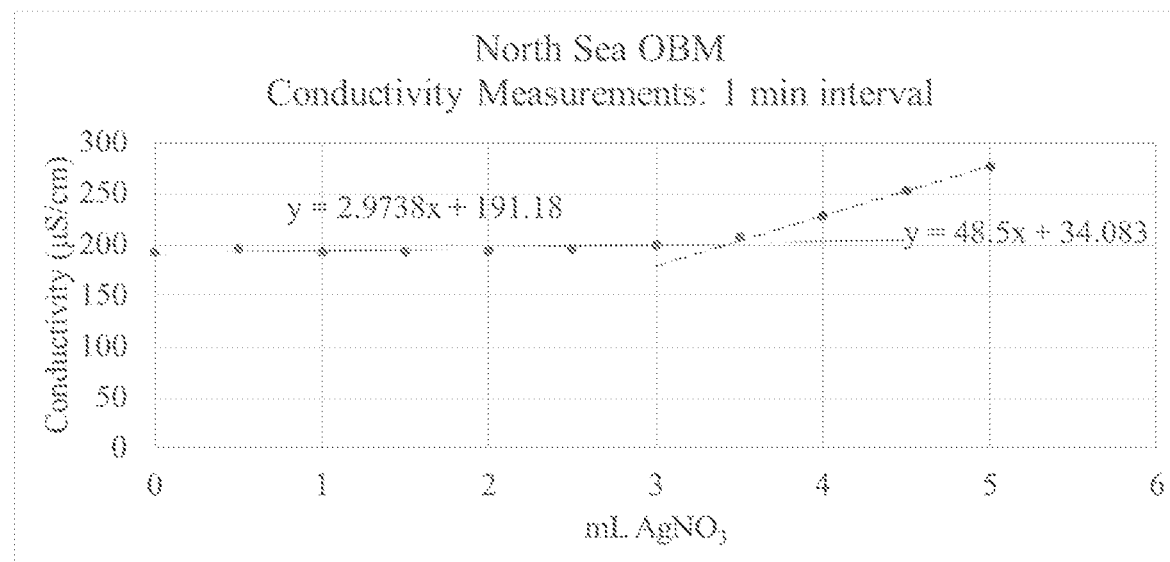
FIGS. 1a and 1b are graphs of results from Example 1, showing intersection of two sets of data to provide an end point.
Figure 1B:
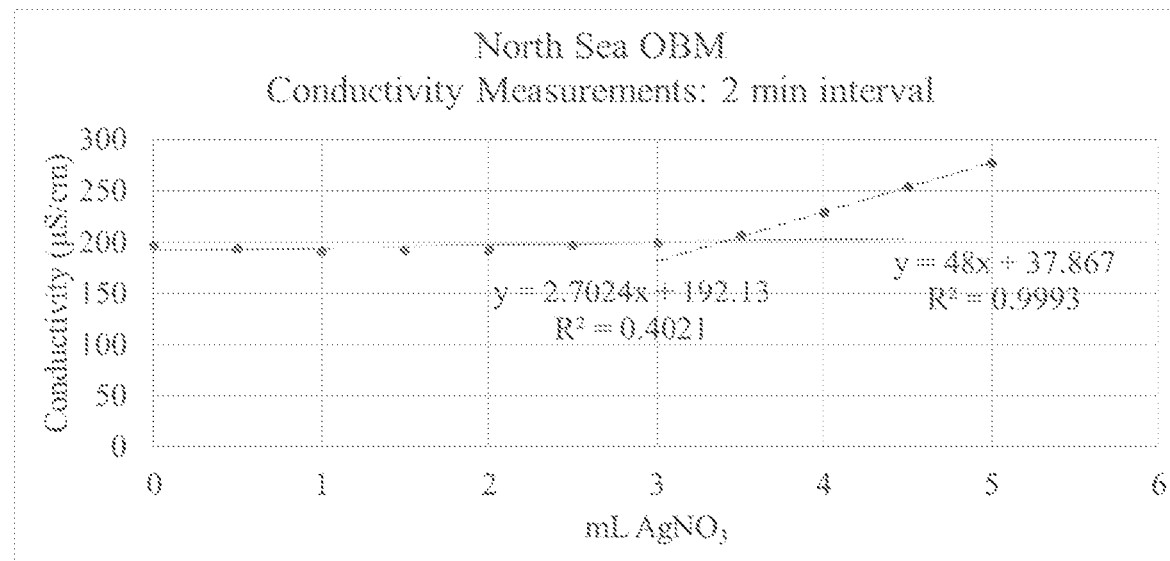
Figure 2A:
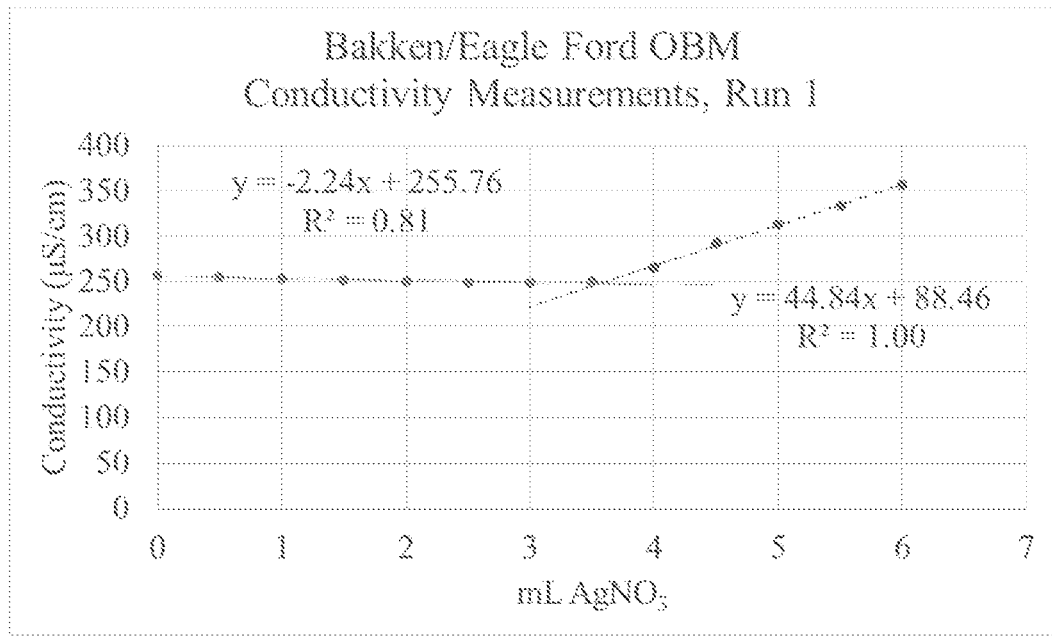
FIGS. 2a and 2b are graphs of results from Example 2.
Figure 2B:
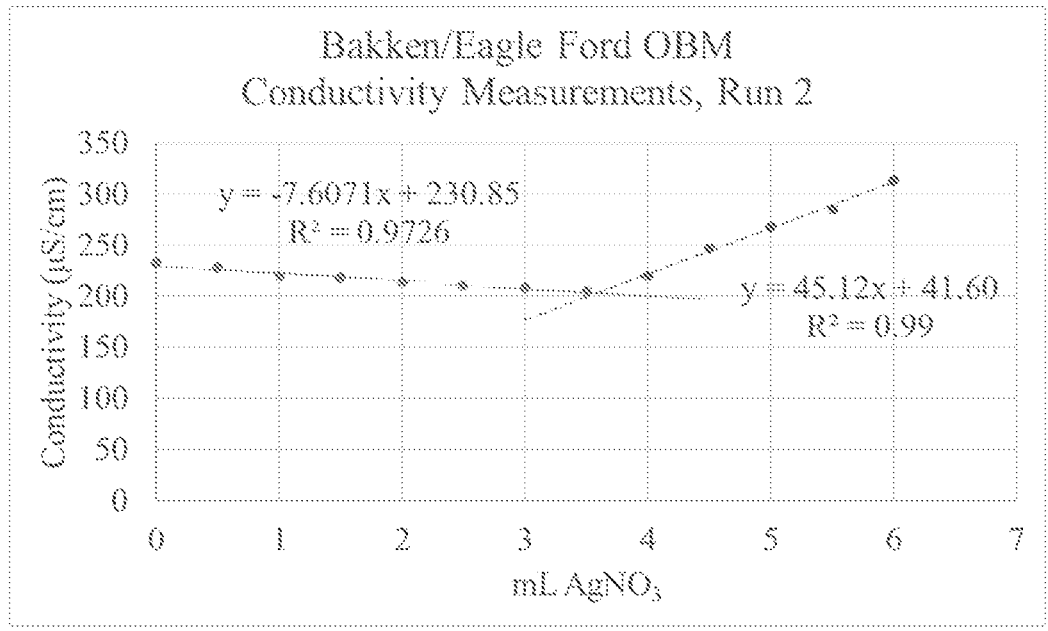

These results are presented graphically in FIGS. 1a and 1b. The final results are presented in Table 3 below.

TABLE 3

Final Results North Sea

| | 1 min | 2 min |
|---|---|---|
| mL AgNO$_3$ | 3.45 | 3.4 |
| mol AgNO$_3$ | 0.282 | 0.282 |
| mL Sample | 2 | 2 |
| Cl$^-$ mg/L | 17,250 | 17,000 |

Comparable results were achieved using the conductivity probe to measure the concentration of chloride versus the standard API method of titrating with a color changing indicator solution. Repeat testing using the same 0.5 mL increments and 1-2 minute measurements yielded similar results.

A test conducted to determine if the amount of time between taking conductivity measurements could be shortened while still giving comparable results: a 30 second interval test was used and it was determined that 30 seconds was not long enough for the sample and titrant to come to equilibrium. the decision was made to stay with the 1 minute interval that had proven to be as effective as 2 minutes in previous testing.

Example 2—Eagle Ford/Bakken Oil Based Mud

A field sample of a mud type known as from the Eagle Ford and Bakken fields in the USA was tested. A sample of this mud was measured via standard titration and the conductivity probe method. Results were compared to the chloride value reported in the field (titration method). Considerable difficulty was noted in determining a color change with the potassium chromate indicator for this mud.

Results of the conductivity test with the oil-based system from the Eagle Ford/Bakken show that the values generated are within 12% error of the value generated from standard titration in the laboratory. However, the difference between conductivity generated values and that of the field titration is 25% error, showing the inaccuracy with the standard color change titration when using the current industry standard potassium chromate method.

Two titrations were conducted and the results shown in Table 4 below.

TABLE 4

Eagle Ford/Bakken Oil-Based System

| mL AgNO$_3$ | Conductivity, μS/cm | Conductivity, μS/cm |
|---|---|---|
| 0 | 256.6 | 232.5 |
| 0.5 | 255.4 | 228.5 |
| 1.0 | 253.6 | 220.3 |
| 1.5 | 251.5 | 218.9 |
| 2.0 | 250.0 | 214.7 |
| 2.5 | 248.7 | 211.2 |
| 3.0 | 248.5 | 208.7 |
| 3.5 | 250.4 | 205.5 |
| 4.0 | 265.2 | 220.4 |
| 4.5 | 293.5 | 247.5 |
| 5.0 | 313.6 | 268.2 |
| 5.5 | 333.9 | 285.9 |
| 6.0 | 357.1 | 314.0 |

The final results are shown in Table 5 below.

TABLE 5

| | Results Eagle Ford/Bakken | |
|---|---|---|
| mL AgNO$_3$ | 3.6 | 3.6 |
| mol AgNO$_3$ | 0.282 | 0.282 |
| mL Sample | 2 | 2 |
| Cl$^-$ mg/L | 18,000 | 18,000 |

The examples above are laboratory procedures using manual probes. The manual procedure is in principle feasible for use in the field, but it is preferable to use an automatic titration apparatus. Apparatus such as the auto titrator produced by a large number of commercial providers including LABTRONICS®, METTLER-TOLEDO®, HIRSCHMANN-OPUS®, THERMO-SCIENTIFIC®, HANNA®, COLE-PARMER®, METROHM®, and others. One example from METROHM® (www.metrohm.com/en-us/products-overview/titration/eco-titrator/210083010) would be suitable to perform the analysis in a way which would free up an operator's time, but is a piece of equipment designed for use in a laboratory not on an offshore oil platform. The inventors believe that, by adaptation of equipment such as this by the provision of suitable protective casings and robust screens and controls, it would be possible to produce a piece of apparatus suitable for use in the field.

Using automatic titration apparatus with conductivity probes will, in the inventors' view, address the problems of a toxic chemical indicator and a color change which can be hard to observe in the field. In one embodiment, the automatic titrator may be a field titrator having a durable case and reagents prepared for use in a remote location. In another embodiment, the automatic titrator may have an automatic sampler and be configured to retrieve and process samples automatically from a container in a laboratory, a mud logging trailer, or other location where analysis may be conducted. The sample location may be connected to or integrated with drilling equipment including but not limited to a stand pipe, mud pump, mud pit, shaker table, mud systems trailer, water processing trailer, or other oilfield equipment.

An automatic titration apparatus may have several components that may be stored in a computer readable media (e.g., memory) and executed on a processing system. The processing system may include instructions that may be executed in an operating system environment, such as a MICROSOFT WINDOWS™ operating system, a LINUX® operating system, or a UNIX® operating system environment. The computer readable medium includes volatile media, nonvolatile media, removable media, non-removable media, and/or another available medium. By way of example and not limitation, non-transitory computer readable medium comprises computer storage media, such as non-transient storage memory, volatile media, nonvolatile media, removable media, and/or non-removable media implemented in a method or technology for storage of information, such as computer readable instructions, data structures, program modules, or other data. The processing system may also utilize a data source of the computer readable media for storage of data and associated information. In one embodiment, data from the automated titration apparatus may be transmitted to a central location for analysis, processing, and modeling. In another embodiment the automated titrator may perform titrations, blanks, probe cleaning, probe calibration and determine concentration.

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

REFERENCES

All of the references cited herein are expressly incorporated by reference. The discussion of any reference is not an admission that it is prior art to the present invention, especially any reference that may have a publication data after the priority date of this application. Incorporated references are listed again here for convenience:
1. API Recommended Practice for Field Testing Oil-Based Drilling Fluids 13B-2, $5^{th}$ edition, 2014
2. www.metrohm.com/en-us/products-overview/titration/eco-titrator/210083010

The invention claimed is:

1. A process for measuring the concentration of chloride in drilling fluid, where the process comprises:
   a) titrating a sample of drilling fluid against silver nitrate;
   b) measuring conductivity of the sample; and
   c) determining chloride concentration based on conductivity of the drilling fluid as silver nitrate is progressively added;
   wherein chloride concentration is determined by observing change in slope of a line showing conductivity versus added silver nitrate.

2. The process according to claim 1, wherein the drilling fluid is oil based or synthetic based drilling fluid.

3. The process according to claim 1, wherein the slope of conductivity versus added silver nitrate is determined before and after an approximate minimum value for conductivity, and a more accurate value of conductivity determined by determining, graphically or mathematically, an intersection of extrapolated plots of conductivity versus silver nitrate.

4. The process according to claim 1, comprising performing the titration using a conductivity probe comprising a polymer or metal protective body and at least one conductivity-detecting sensor within the protective body.

5. The process according to claim 4, wherein the sensor or a major portion of the sensor comprises a substantially flat plate.

6. The process according to claim 1, wherein the drilling fluid sample is stirred or agitated during the titration.

7. The process according to claim 1, wherein the drilling fluid sample is allowed to reach equilibrium for a period selected from between 15 and 180 seconds, between 45 and 180 seconds, between 60 and 120 seconds, at least 15 seconds, at least 30 seconds, at least 45 seconds, at least 60 seconds, at least 75 seconds, at least 90 seconds, at least 105 seconds, at least 120 seconds, at least 135 seconds, at least 150 seconds, at least 165 seconds, and at least 180 second after adding each aliquot.

8. The process according to claim 1, comprising performing the titration using an automatic titration apparatus.

9. The process according to claim 8, wherein the automatic titration apparatus performs the following steps:
   i. adding a predetermined aliquot of silver nitrate solution to the drilling fluid sample;

ii. after the addition of an aliquot, allowing the sample to equalize for a predetermined period or until an equilibrium conductivity value is obtained;
iii. taking a reading from a conductivity probe in the sample;
iv. repeating steps i)-iii) until an approximate end point is achieved,
v. plotting the conductivity reading against total added silver nitrate before and after the approximate end point; and
vi. mathematically determining an accurate end point based on calculated values of slope before and after the end point.

10. The process according to claim 9, wherein the automatic titration apparatus, in step (ii), stirs or agitates the sample.

11. The process according to claim 9, wherein, in step (ii), the sample is allowed to equalize for a period selected from between 15 and 180 seconds, between 45 and 180 seconds, between 60 and 120 seconds, at least 15 seconds, at least 30 seconds, at least 45 seconds, at least 60 seconds, at least 75 seconds, at least 90 seconds, at least 105 seconds, at least 120 seconds, at least 135 seconds, at least 150 seconds, at least 165 seconds, and at least 180 second after adding each aliquot.

12. The process according to claim 1 including, prior to performing steps a) to c), performing an intermediate titration on a sample of drilling fluid to provide an indication of calcium concentration and thereby an approximate indication of chloride concentration.

13. The process according to claim 12, wherein the intermediate titration is performed using a calcium chelating agent.

14. The process according to claim 12, wherein the intermediate titration is performed using automatic titration apparatus.

* * * * *